United States Patent [19]

Nieschulz et al.

[11] 4,031,199
[45] June 21, 1977

[54] PROCESS FOR THE PRODUCTION OF ALLERGEN-CONTAINING EXTRACTS

[75] Inventors: Otto Nieschulz, Hamburg; Günther Rüdiger, Reinbek; Jürgen Maass, Kroeppelshagen, all of Germany

[73] Assignee: Merck Patent Gesellschaft mit beschrankter Haftung, Darmstadt, Germany

[22] Filed: Dec. 15, 1975

[21] Appl. No.: 640,546

Related U.S. Application Data

[62] Division of Ser. No. 421,791, Dec. 5, 1973, Pat. No. 3,953,588.

[30] Foreign Application Priority Data

Oct. 20, 1973 Germany .......................... 2352724
Dec. 11, 1972 Germany .......................... 2260455

[52] U.S. Cl. .................................. 424/12; 424/3; 424/88; 424/89; 424/91; 424/92; 241/1; 241/2

[51] Int. Cl.² ..................................... A61K 39/100

[58] Field of Search ............. 424/3, 12, 88, 89, 91, 424/92; 241/2, 1

[56] References Cited

UNITED STATES PATENTS

| 2,738,172 | 3/1956 | Spiess, Jr. ............................ 241/1 |
| 3,553,311 | 1/1971 | Smith ................................. 424/12 |
| 3,558,066 | 1/1971 | Alliger ................................ 241/2 |

OTHER PUBLICATIONS

Remington's Pharmaceutical Sciences, 13th ed., pp. 486–488, Mack Publishing Co., Easton, Pa, (1965).

Primary Examiner—Donald B. Moyer
Attorney, Agent, or Firm—Milen & White

[57] ABSTRACT

Improved allergen-containing extracts are obtained by the extraction of allergy-causing materials, such as pollen and house dust, with hydrophilic aqueous extractants, by pretreating the allergen-containing material with a lipophilic, aqueous extraction liquid. Allergens extracted in the two steps can be combined and formed into allergen preparations, which can be used both for diagnostic and therapeutic purposes.

6 Claims, No Drawings

PROCESS FOR THE PRODUCTION OF ALLERGEN-CONTAINING EXTRACTS

This is a division of application Ser. No. 421,791 filed Dec. 5, 1973, now U.S. Pat. No. 3,953,588.

BACKGROUND OF THE INVENTION

This invention relates to a novel process for the production of allergen-containing extracts and to preparations produced therefrom suitable for the diagnosis of sensitizing antigens and for the specific desensitization of allergic persons.

It has long been known that many persons show allergic reactions upon contact with certain naturally occurring materials. Carriers of such allergenically active agents include pollens, seeds, epithelia, especially animal hairs, dusts, especially house dust, insects, and fungi.

Clinical experience has shown that allergic reactions can be lessened by subcutaneous injections of extracts of the substances causing the allergy. Heretofore, aqueous liquids, such as physiological NaCl solution, weakly alkaline, optionally buffered salt solutions, and dilutions of alcohol in physiological NaCl solutions have been employed for the production of such allergenic extracts or preparations in general, sometimes after previously degreasing the allergen-containing starting material with ether.

Generally, the thus-obtained solutions, after removal of the solid components, are filtered aseptically and injected suitably diluted into the patients for desensitizing purposes. The use of these aqueous extracts requires a larger number of injections with gradually increasing amounts of allergen. Therefore, the use of semidepot preparations is advantageous, permitting a substantial reduction of the number of injections required and simultaneously lessening the danger of excessive reaction. The literature has described extraction processes for the production of such semidepot preparations using aqueous solutions of heterocyclic tertiary amines, especially pyridine, lutidine and quinoline.

The binding of the extracted allergens is accomplished as an aluminum hydroxide adsorbate by adding alum solution to the alkaline extract. The thus-formed precipitate containing the active substances is resuspended in a physiological solution after removal of the solvent and after repeated washing. However, these semidepot preparations can be utilized only for the treatment of patients and not for diagnostic purposes. Such preparations are, for example, described in the U.S. Pat. Nos. 3,148,121 and 3,148,122.

OBJECTS OF THE INVENTION

It is an object of this invention to provide a novel process for the production of improved allergen-containing extracts and preparations from allergen-containing materials by which it is possible to obtain, from the same allergen-containing material, allergenic materials useful both in test solutions for the diagnostic skin testing procedure and in aqueous treatment extracts and semidepot preparations for therapy purposes.

Another object is to provide the novel extracts and preparations thus produced.

Upon further study of the specification and appended claims, further objects and advantages of this invention will become apparent to those skilled in the art.

SUMMARY OF THE INVENTION

According to this invention allergen-containing extracts are produced in an extraction process wherein a multiple allergen-containing allergy-causing material is extracted with a hydrophilic aqueous extractant which comprises subjecting the allergen-containing material, prior to the extraction with the hydrophilic aqueous extractant, to a pretreatment with a lipophilic, aqueous extraction liquid containing an essentially neutral, water soluble organic solvent and sonicated to increase allergenic activity.

DETAILED DISCUSSION

This novel two-step process is based on the fact that the naturally occurring allergen-containing materials, e.g., pollens, dusts, epithelia, fungi, insects, etc., generally contain several allergens, which differ one from another with respect to their solubility in aqueous and lipophilic aqueous solutions. These naturally occurring materials are characterized by comprising cellular material and containing a plurality of allergens, a portion of which is more lipophilic in character than the remainder.

The extracts obtained in the two separate treatment steps are then preferably combined and, if desired, processed into novel allergen preparations in a conventional manner. Alternatively, the allergenic material extracted in only one of the steps, preferably the last, can be employed.

It was found that the novel extraction process of this invention has considerable advantages over conventional extraction processes. Thus, for example, the denaturing of the allergens which normally occurs during the extraction for the most part can be avoided. An essential factor to achieve this end is the gentle extraction method provided by this invention, using the well-proven prior art aqueous extraction solution in combination with a pretreatment employing an aqueous mixture comprising a lipophilic organic, water-miscible solvent. Such an organic solvent is required, since those allergens which are difficult to dissolve in water and aqueous-alcoholic solutions should be extracted as completely as possible. The organic solvents heretofore employed for extracting purposes, e.g., pyridine, cannot be removed from the extracts without the utilization of elevated temperatures. Such elevated temperatures and also the character of the solvents can cause a change or denaturing of the allergens. Furthermore, the pyridine normally becomes bound very firmly, partially also in a complex form, so that a complete removal of this extractant causes considerable difficulties.

Diethyl ether has heretofore been employed for a pretreatment of the allergen-containing materials, especially for degreasing purposes. Although this treatment is employed to eliminate undesired lipoids and lipids, presumably allergenically active agents are also extracted. However, the diethyl ether fraction heretofore was discarded. In any event, the diethyl ether heretofore employed is furthermore incapable of dissolving lipoids blocked by water barriers.

When conducting the extraction process of this invention, allergens having different solubility characteristics are extracted in a very gentle manner, and the various components of the allergen-containing starting material are obtained. Surprisingly, the yield of the components extractable with the usual aqueous extractants is considerably increased by the pretreatment with the lipophilic aqueous extraction liquid in accordance with this invention. The novel process of this invention also has essential advantages over the extraction method described in German Unexamined Laid-Open Application DOS No. 2,003,117, according to which, in the first reaction step, an extraction is effected with the customary aqueous extraction liquids, and thereafter an extraction is conducted with an organic solvent, e.g., pyridine. Whereas the allergens are altered when conducting the conventional extraction process, due to the properties of the organic liquids (especially the strongly polar and basic nature thereof), the allergens are not denatured by the method of this invention. Rather, the allergens are extracted more completely and more gently. For this reason, the novel process yields extracts which provoke a stronger allergenic reaction in the skin test and thus are better suited for diagnostic purposes. Besides, according to the process employing pyridine, there is extracted greater amounts of those components of the allergen-containing materials which primarily do not have an allergenic significance, but which can evoke, by injection during the treatment, an undesired sensitization. By the more gentle extraction in accordance with the present invention, no completely water-insoluble components are dissolved, in contrast to the literature process employing pyridine, due to the complex formation which occurs. The treatment with the lipophilic aqueous extraction liquid (pretreatment stage according to this invention) is not an exhaustive extraction of the water-insoluble substances, but is primarily a pretreatment to facilitate the subsequent extraction with the conventional aqueous liquids, which latter procedure than takes place surprisingly in an optimum manner. However, this pretreatment also serves to extract the allergens with lipophilic groups which are difficult to dissolve in water, which allergens are essentially not denatured by the extremely gentle extraction method and are thus obtained with unreduced allergenic activity. The essential aspect of the process of this invention is that extracts and/or solutions are produced for the first time which truly contain an identical spectrum of allergenic components, both in the aqueous test solutions and in the semidepot preparations required for therapy. In contrast, in the extracts obtained by the conventional two-stage process, the water-insoluble components are precipitated during the dilution required for the test solutions, whereas they remain in the semidepot preparations as a constituent thereof.

The term lipophilic aqueous extraction liquid means an aqueous extracting liquid containing a sufficient amount of an organic solvent for lipophilic materials to render the aqueous-organic mixture an extracting liquid for the lipophilic materials present in small amounts in allergy-causing naturally occurring materials. Such an organic solvent must meet several criteria in order to be suitable for the process of this invention. First, it should be water soluble, i.e., miscible with the aqueous, inorganic portions of the extracting liquid, at least in the proportion employed. In order to be readily removed from the allergens extracted with the extracting liquid, it ought have a boiling point below 105° C, preferably below 70° C. Also, to avoid complexing with the allergenic proteins, it ought be essentially neutral, i.e., neither a Bronsted acid nor a base, e.g., an amine. Examples of suitable such organic solvents are the water-soluble cyclic ethers having boiling points below 105° C, e.g., tetrahydrofuran tetrahydropyran, dioxane.

The term "lipophilic" is used herein in the conventional sense, i.e., essentially water repelling and attracted to rather than repelled by solvents for fats and oils.

The preferred cyclic ethers employed in the pretreatment step in accordance with the process of this invention possess excellent solubility properties. They can be employed in mixtures with water over a wide ratio without losing their lipophilic properties, even in a considerable aqueous dilution. Furthermore, they are chemically inert and, due to their relatively low boiling point, can be readily removed from the extracts by evaporation. For this reason, tetrahydrofuran is also preferred over the solvents tetrahydropyran and dioxane, which are also well suitable. Due to their miscibility with water, these solvents also extract lipoids and lipophilic allergens blocked by water barriers and optimally prepare the allergen-containing starting material for the aqueous extraction in the second step.

The lipophilic aqueous extracting liquid, which preferably contains as the organic solvent for lipophilic materials a cyclic ether having a boiling point below 105° C, is a mixture of the organic solvent with water or with aqueous ammonia, preferably in a volume ratio of about 5 : 1 to about 1 : 2, preferably about 1 : 1. The aqueous, i.e., inorganic water portion, of the extracting liquid advantageously contains about 1–10%, preferably about 5%, by weight of $NH_3$. Especially suitable are extracting liquids wherein a cyclic ether, water and concentrated ammonia (25% strength) in the ratio of about 5 : 4 : 1, i.e., the organic and inorganic portions are present in about a 1 : 1 ratio and the ratio of water to $NH_3$ is about 16 : 1. However, in many cases, the proportion of ammonia can also be substantially lower so that the extraction also can be conducted, with a mixture as defined above, in a ratio of 10 : 8 : 1, i.e., a cyclic ether, water, $NH_3$ ratio of 40 : 32 : 1. The pH of the lipophilic extractant is, when ammonia is present, generally and advantageously between about 11 and 12.

The amount of lipophilic aqueous extraction liquid employed is not critical and can vary widely. Generally at least about 3 ml., preferably about 10 to 100 ml., per g. of allergen-containing starting materials is employed.

The pre-extraction is conducted in the conventional manner. The allergen-containing naturally occuring material, which preferably has previously been comminuted and/or ground up, is mixed with the lipophilic aqueous extraction liquid and allowed to stand several hours, e.g., 5–60 hours, and/or it is shaken in a vibrator. Suitably, the extraction is preferably effected at about room temperature, although basically the process can also be accomplished at lower temperatures, e.g., 0°–20° C. Thereafter, the undissolved solid components are separated from the liquid, e.g., by centrifugation, decantation or filtration. These steps can be repeated, if desired. The separated liquid phase is concentrated under gentle conditions, e.g., at room temperature and optionally at reduced pressure to remove the organic solvent or evaporated completely to dryness. This is done, for example, advantageously using a rotary evaporator with waterbath temperatures not exceeding approximately 40° C. The thus-obtained residue is the final product of the pretreatment step.

The residual allergen-containing undissolved solids, prepared and partially extracted in the pretreatment step with the lipophilic aqueous extraction liquid are then subjected, in a second step, to a customary extraction with a conventional hydrophilic aqueous extractant.

The term "hydrophilic aqueous extractant" means a completely aqueous, an aqueous-alcoholic, or a like aqueous extracting liquid which is essentially a non-solvent for lipophilic materials. This means that any organic solvent, e.g., methanol or ethanol, which is either essentially a non-solvent itself for lipophilic materials or is present in an amount insufficient to render the aqueous mixture comprising it, a solvent for lipophilic materials. For example, the preferred tetrahydrofuran present in the lipophilic aqueous extraction liquid employed in the pretreatment step can be present, instead of or in combination with the alcohol conventionally employed, in amounts small enough, e.g., about 1 – 8% by volume, not to significantly affect the basic hydrophilic characteristics of the aqueous, non-organic portion of the extraction liquid.

The term "hydrophilic" is used herein in the conventional sense, i.e., a substance which is water attracting rather than water repelling.

Summaries of the extraction liquids used in such process can be found, for example, in "Konstitution, allergische Krankheiten, Krankheiten der Knochen, Gelenke und Muskeln" (Constitution, Allergic Diseases, Bone, Joint, and Muscle Diseases) prepared by F. Curtius et al., Springer Verlag (publishers) 1954, pp. 389–392, as well as in the "Journal of Allergy" vol. 30, 1959, pp. 66–82, whose disclosures are incorporated by reference. Thus, in particular, suitable are physiological NaCl solutions, salt-containing buffer solutions, 12% strength ethanol, or Cocas solution which contains, in 100 ml. of solution: 0.5 g. of NaCl, 0.25 g. of $NaHCO_3$, and 0.4 g. of phenol.

The amount of hydrophilic aqueous extractant employed is not critical and can vary widely. Generally, at least about 3 ml., preferably about 10 to 100 ml., per g of allergen-containing starting material is employed.

As in the pretreatment step, the undissolved solids are then separated from the extracting liquid in a conventional manner, preferably by centrifuging, and preferably at about room temperature. It is sometimes advantageous to regulate the extraction in this second stage so that the thus-produced, separated aqueous phase is obtained as a physiologically adjusted salt solution.

In this way, essentially all water-soluble allergens present in the allergen-containing materials are extracted.

It has proved to be very advantageous to combine the extracts obtained in the two extraction steps. In this manner, an extract is obtained which contains essentially all of the allergenically effective components of the allergen-containing starting material. It is particularly advantageous to first free the extract obtained in the first stage from the organic solvent and to combine the thus-produced aqueous or solid residue, depending on whether the water is also removed, with the extract obtained in the second stage. In this way, a stock extract of high allergenic activity is produced which is free of organic solvent. This extract is subsequently further treated in the usual manner, i.e., filtered, for example, via membrane diaphragm filters first for clarity and then aseptically to render it suitable for clinical use. For preservation purposes, about 0.4% of phenol can, as usual, also be added. Such an extract is then equally well suitable for the production of diagnostic preparations as well as therapeutically usable preparations. The thus-obtained extract containing the combined allergens with differing solubility characteristics can now be utilized in a conventional manner, viz., like the heretofore known allergen extracts. Thus, it is possible, for example, by dilution, e.g., with physiological NaCl solution or with Cocas solution, to obtain extracts suitable for testing purposes. Also, provocation test solutions can be prepared therefrom in a conventional manner. Furthermore, the same stock extract can be utilized for producing without difficulty injectable solutions suitable for therapy in accordance with standard methods, in desired dilutions adapted to the respective treatment goal.

Further, this combined extract is suitable for the production of so-called semidepot preparations produced in accordance with methods known from the literature with the aid of aluminum hydroxide. In this procedure, the alkalinized extract is mixed with an aluminum salt solution, e.g., alum, and aluminum hydroxide is precipitated by changing the pH value. The thus-obtained precipitate settles as a sediment. The supernatant liquor is clear and only slightly discolored, while the aluminum hydroxide adsorbate has a distinct color which is characteristic of the respective extract. The supernatant, clear solution is filtered by suction, and the suspension is washed very thoroughly with a solution consisting in most cases of a physiological NaCl solution with 0.4% of phenol. By dilution with sterile physiological NaCl solution to the desired PNU protein-bound nitrogen content, a preparation suitable for therapy is then obtained.

All operations are to be effected with sterile solutions and in sterile apparatus in a closed sytem.

As disclosed and claimed in our copending application Ser. No. 421,817 filed Dec. 5, 1973, and now U.S. Pat. No. 3,953,342 very advantageous to subject both the insoluble and dissolved solids of the allergen-containing starting material to an ultrasonic treatment at some stage during the manufacturing of the allergen-containing extracts and preparations. The ultrasonic treatment can be effected at any desired stage of the manufacturing process, but an ultrasonic treatment during or after the second extraction stage is preferred. This provides the special advantage that a long-term extraction can be avoided. In the heretofore customary extraction methods, relatively long extraction periods must be tolerated, for example normally 1–10 days. In this connection, there is always the possibility that chemically or microbiologically triggered changes occur in the allergens and allergen carriers.

By means of the extraction with simultaneous ultrasonic treatment, the extraction periods can be quite considerably reduced. In accordance with a preferred embodiment of this invention, it is sufficient to subject the insoluble solids of the starting material, together with the extraction liquid, to an ultrasound treatment for a few minutes, in order to attain a good extraction. In many cases, it is suitable to subdivide larger amounts of liquid into smaller portions for the ultrasonic treatment. Normally, it is sufficient to conduct the ultrasonic treatment for about 0.5 – 5 minutes. Low-frequency ultrasound is preferably utilized, for example in a frequency range of about 20–30 kilohertz, preferably about 20–25 kilohertz.

The mixture is advantageously cooled during the ultrasonic treatment, e.g, with ice water, so that the solution is not heated up by the ultrasonic treatment. In addition to a drastic shortening of the required extraction time, e.g., to about 0.5 to 5, preferably about 2 to 3 minutes, the thus-attained considerable increase in the yield of allergen-active material is of particular advantage. Moreover, in this way, a bacterial and mycotic contamination of the allergen-containing starting material is inhibited.

Surprisingly, the level of effectiveness of the thus-produced allergen extracts is substantially increased. Also the yield of protein-bound nitrogen (PNU) in the final extract is increased up to 100% by this additional ultrasonic treatment.

Even if only the extracted solids obtained in the extraction process of this invention or solutions prepared therefrom by the usual dilution, and not the insoluble solids, are treated subsequently with ultrasound, the allergenic effectiveness of the final extract is extensively increased. The ultrasonic treatment effects generally, as compared to the untreated extract, an increase in the allergen potency up to about tenfold. Here again, the procedure is advantageously conducted while cooling with ice water to avoid denaturing the proteins in the solution. The point during the overall process when ultrasonic treatment is conducted can be selected arbitrarily, as mentioned above. However, it suitably is conducted prior to dispensing of the extracts into their product package, e.g., ampoules.

The novel process thus makes it possible to produce especially highly effective allergen extracts and preparations which are clearly superior to those known heretofore. The extracts and preparations are utilized in allergic diseases for diagnosis and therapy in the same manner as the extracts and preparations previously available.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error. All ratios are by volume.

EXAMPLE 1

9 g. of the pollens of *Festuca elatior* (fescue) was ground in a ball mill for 16 hours. The ground pollen material was mixed in an Erlenmeyer flask having a capacity of 1 liter with 300 ml. of a mixture of tetrahydrofuran: water: concentrated ammonia (25%) in a ratio of 5 : 4 : 1, and shaken in a vibrator for 16 hours at room temperature. By centrifuging at 4,500 r.p.m., the undissolved solid components were separated from the effluent (Extract I).

The sediment from the above step was suspended in 200 ml. of Cocas solution (Cocas solution contains, in 100 ml. of solution: 0.5 g. of NaCl, 0.25 g. of $NaHCO_3$, and 0.4 g. of phenol), diluted with water in a ratio of 1 : 1 . The suspension was divided into three portions. Each portion was treated for 3 minutes with ultrasound having a frequency of 22 kilohertz and a maximum power of 150 watts, under ice water cooling. The three portions were again combined and the residual sediment separated by centrifuging from the effluent (Extract II).

Extract I was evaporated to dryness in a rotary evaporator at a water-bath temperature of 35° C and at about 10 torr (mm. Hg). The residue was dissolved in 10 ml. of 1N NaOH, the solution was neutralized with 10 ml. of 1N HCl, and this solution was again evaporated to dryness in the rotary evaporator.

The thus-produced dry residue was dissolved in Extract II. The solution was aseptically filtered successively, via membrane filters with different pore widths in a pressure filtration device, and finally with a membrane filter.

In this way, 270 ml. of a green, turbid stock extract was obtained containing 51,900 PNU/ml., corresponding to a total PNU yield of 1,557,000 PNU/g. of pollen material.

A portion of the thus-obtained stock extract was diluted with undiluted Cocas solution directly to an extract suitable for skin testing, the solution being set according to standard to 100 PNU/ml. Prior to use, this extract is further diluted as necessary, normally by at least two powers of ten.

A further portion of the stock extract was diluted, for the preparation of a provocation test solution, with undiluted Cocas solution to a PNU content of 5,000 PNU/ml.

For the production of a semidepot preparation, a third portion of the stock extract was brought to 20,000 PNU/ml. with demineralized, sterile water. The semidepot preparation was produced as follows:

The adsorptive binding of the allergens to an active aluminum hydroxide was accomplished by precipitation with an aluminum salt solution. For this purpose, 200 ml of a 2% potassium aluminum alum solution in 0.25N $H_2SO_4$ was added to 180 ml. of the extract solution, which had been mixed with 20 ml. of concentrated (25%) aqueous ammonia solution. The mixture was then vigorously agitated. Thereafter, the mixture was dialyzed against tap water for 24 hours and against demineralized water twice, for one hour, respectively. The aluminum hydroxide adsorbate showed a very pronounced greyish-green color. The supernatant, clear solution was vacuum-filtered, and the suspension was washed repeatedly with a solution containing 0.9% of sodium chloride and 0.4% of phenol.

All operations were conducted with sterile solutions and in sterile apparatus in a closed system. In this way, 300 ml. of adsorbate suspension containing 14,400 PNU/ml. was obtained, corresponding to a yield of 80%, based on the PNU units initially employed. The suspension was brought to a content of 10,000 PNU/ml. by dilution with sterile physiological NaCl solution. A subsequently conducted examination as to sterility showed asepsis. This solution was found useful for administration by injection.

EXAMPLE 2

9 g. of pollens of *Dactylis glomerata* (orchard grass, cockspur) was ground for 16 hours in a ball mill with porcelain balls. The pollen material was extracted analogously to Example 1, except in contract thereto, with a solvent mixture of dioxane : $H_2O$ : concentrated (25%) ammonia in a ratio of 5 : 4 : 1. In the second extraction step, instead of the water-diluted Cocas solution, Evans solution, also diluted in the same ratio, was utilized.

(Evans solution: 5.0 g. NaCl, 0.36 g. $KH_2PO_4$, 4.0 g. phenol, and 7.0 g. $Na_2HPO_4$ in 1000 ml. of distilled water.)

The ultrasonic treatment was conducted in the same manner, by subjecting the extraction solution containing suspended undissolved solids to ultrasound in three portions for a duration of 3 minutes. The thus-obtained combined stock extract had a total volume of 240 ml. and exhibited a brownish-green color. The yield was 41,500 PNU/ml., corresponding to a total PNU content of 1,106,700 PNU/g. of pollen material utilized. The precipitation and the binding to aluminum hydroxide were effected as described in Example 1. 300 ml. of an aluminum hydroxide adsorbate suspension was obtained with a content of 12,700 PNU/ml., corresponding to a PNU yield of 70.5%.

EXAMPLE 3

Analogously to Example 1, 9 g. of pollens of Secale cereale (rye) was extracted. However, in place of tetrahydrofuran, the same amount by volume of tetrahydropyran was employed in the first extraction stage. The product was an aluminum hydroxide adsorbate having a specific content of 13,500 PNU/ml. of suspension. 300 ml. of this suspension thus corresponded to a total content of 3.99 million PNU (73.9% yield).

Corresponding results are obtained with the following allergen-containing materials: house dust, *Mucor mucedo* (mold fungus), bed feathers (consisting predominantly of goose feathers), and honeybees, killed at a low temperature.

EXAMPLE 4

House dust, collected by means of a vacuum cleaner, was screened through a series of test sieves. Only the fraction passing a screen having a mesh width of 0.3 mm. was utilized for extraction, in order to retain wool and hairs.

70 g. of screened house dust was combined, in a 1-liter Erlenmeyer flask, with 300 ml. of a mixture of tetrahydrofuran : water: concentrated (25%) ammonia in a ratio of 5 : 4 : 1, and shaken for 16 hours in a vibrator. By centrifuging at 4,500 r.p.m., the solid components were separated from the effluent (Extract I). The sediment was suspended with 300 ml. of a Cocas solution diluted with water in a ratio of 1 : 1, and extracted, with occasional shaking, three times alternatingly for 8 hours at 45° C and then for 8 hours at room temperature. By centrifuging at 4,500 r.p.m. the sediment was separated from the effluent (Extract II).

Extract I was evaporated in a rotary evaporator at a water-bath temperature of 36° C and under 10 torr until a dry substance was obtained. The residue was dissolved in 10 ml. of NaOH, the solution was neutralized with 10 ml. of 1N HCl, and again evaporated to dryness in the rotary evaporator. The thus-obtained dry residue was dissolved in Extract II. The solution was filtered successively via membrane filters of varying pore widths in a pressure filtration device so that a clear product was obtained and subsequently so that a sterile product was obtained.

In this way, 270 ml. of a clear, dark-brown stock extract was obtained with 60,000 PNU/ml. corresponding to a total PNU yield of 240,000 PNU/g. of house dust employed.

EXAMPLE 5

Analogously to Example 1, 9 g. of pollens of Festuca elatior (fescue) was mixed, after grinding, with 300 ml. of a mixture of tetrahydrofuran and water (1 : 1), and shaken in a vibrator for 16 hours at room temperature. By centrifuging at 4,500 r.p.m., the solid components were separated from the resulting effluent (Extract I).

The sediment was extracted analogously to Example 1, thus obtaining Extract II, which was treated as described therein.

Extract I was brought to dryness, and the thus-obtained dry residue was dissolved in Extract II. The solution was aseptically filtered successively via membrane filters with varying pore widths in a pressure filtration device and finally with a membrane filter.

In this way, 270 ml. of a green, turbid stock extract was obtained with a content of 31,650 PNU/ml., corresponding to a total PNU yield of 950,000 PNU/g. of pollen material.

A portion of the thus-obtained stock extract was directly diluted with undiluted Cocas solution to an extract suitable for skin testing, the solution being adjusted in accordance with the standard to 100 PNU/ml. Prior to use, this extract is further diluted as required, normally by at least two powers of ten.

A further portion of the stock extract was diluted in order to produce a provocation test solution, with undiluted Cocas solution to a PNU content of 5,000 PNU/ml.

In order to prepare a semidepot preparation, a third portion of the stock extract was brought to 20,000 PNU/ml. with demineralized sterile water. For producing the semidepot preparation, the procedure of Example 1 was followed analogously. 300, ml. of adsorbate suspension with a content of 7,590 PNU/ml. was thus obtained, corresponding to a yield of 80% based on the PNU units initially employed. When suspended in isotonic saline solution, an allergenic preparation suitable for administration by injection is obtained.

EXAMPLE 6

9 g. of pollens of Dactylis glomerata (orchard grass, cockspur) was extracted analogously to Example 2 with a solvent mixture of dioxane and $H_2O$ in a ratio of 1 : 1. In the second extraction step, Evans solution was utilized analogously to Example 2. The ultrasonic treatment was conducted analogously to Example 1, by treating the extraction solution with suspended solids in three portions with ultrasound for 3 minutes. The thus-obtained combined stock extract had a total volume of 240 ml. and showed a brownish-green color. The yield was 25,800 PNU/ml., corresponding to a total PNU content of 688,000 PNU/g. of utilized pollen material. The precipitation and the binding to aluminum hydroxide were effected as described in Example 1. 300 ml. of an aluminum hydroxide adsorbate suspension was obtained, with a content of 4,500 PNU/ml., corresponding to a PNU yield of 65%.

EXAMPLE 7

Analogously to Example 5, 9 g. of pollens of Secale cereale (rye) was extracted. However, in place of tetrahydrofuran, the same proportion by volume of tetrahydropyran was utilized. The result was an aluminum hydroxide adsorbate having a specific content of 7,800 PNU/ml. of suspension. 300 ml. of this suspension thus corresponded to a total content of 2.34 million PNU (68% yield).

Corresponding results are obtained with the following allergen-containing materials: house dust, *Mucor mucedo* (mold fungus), bed feathers (consisting primarily of goose feathers), and honeybees, killed at low temperature.

EXAMPLE 8

House dust collected by means of a vacuum cleaner was mixed analogously to Example 4 with 300 ml. of a mixture of tetrahydrofuran and water (volume ratio 1 : 1) Extract II was obtained with Cocas solution.

Extract I was brought to dryness analogously to Example 4. The thus-produced dry residue was dissolved in Extract II. The solution was filtered clear successively via membrane filters with various pore widths in a pressure filtration device and then was filtered aseptically.

In this way, 270 ml. of a clear, dark-brown stock extract with 39,000 PNU/ml. was obtained, corresponding to a total PNU yield of 150,000 PNU/g. of house dust employed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing an allergen extract which includes pre-extracting an allergen-containing material having a plurality of allergens, a portion of which is more lipophilic in character than the remainder, with a lipophilic solvent consisting essentially of an aqueous solution of a neutral, water-soluble cyclic ether having a boiling point below 105° C. which is at least one member selected from the group consisting of tetrahydrofuran, tetrahydropyran and dioxane to extract said lipophilic portion; extracting resultant allergen-containing material with a hydrophilic aqueous or aqueous alcoholic allergen solvent; and recovering water-soluble allergens from said material; the improvement which comprises:

sonicating said allergen-containing material to increase allergenic activity.

2. A process according to claim 1, wherein said allergen-containing material is selected from the group consisting of allergenic pollens, seeds, house dust, epithelia, fungi and insects.

3. A process according to claim 1, wherein ultrasonic sound having a frequency of 20–30 kilohertz is employed.

4. A process according to claim 1, wherein ultrasonic treatment is conducted during extraction with said hydrophilic aqueous or aqueous alcoholic allergen solvent.

5. A process according to claim 1, wherein said allergen-containing material is selected from the group consisting of allergenic pollens, seeds, house dust, epithelia, fungi and insects and ultrasonic treatment is conducted during extraction with said hydrophilic aqueous or aqueous alcholic solvent employing ultrasonic sound having a frequency of 20–30 kilohertz.

6. An allergen-containing extract prepared according to the process of claim 5.

* * * * *